(12) United States Patent
Nagae et al.

(10) Patent No.: US 9,448,100 B2
(45) Date of Patent: Sep. 20, 2016

(54) SIGNAL PROCESSING APPARATUS

(75) Inventors: Kenichi Nagae, Yokohama (JP); Hirofumi Taki, Osaka (JP); Toru Sato, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 553 days.

(21) Appl. No.: 13/981,233

(22) PCT Filed: Feb. 1, 2012

(86) PCT No.: PCT/JP2012/052799
§ 371 (c)(1),
(2), (4) Date: Aug. 26, 2013

(87) PCT Pub. No.: WO2012/105718
PCT Pub. Date: Aug. 9, 2012

(65) Prior Publication Data
US 2013/0338944 A1    Dec. 19, 2013

(30) Foreign Application Priority Data
Feb. 4, 2011  (JP) .................................. 2011-022776

(51) Int. Cl.
*G01F 17/00*   (2006.01)
*G01H 1/00*   (2006.01)
(Continued)

(52) U.S. Cl.
CPC *G01H 1/00* (2013.01); *A61B 8/14* (2013.01); *A61B 8/4488* (2013.01); *A61B 8/483* (2013.01);
(Continued)

(58) Field of Classification Search
CPC . G06F 3/0433; A61B 8/0825; A61B 8/0833; Y10S 367/907; G01S 7/52036; G01S 7/52073; G09B 23/286
See application file for complete search history.

(56) References Cited

U.S. PATENT DOCUMENTS 5,048,936 A * 9/1991 Hatori ..................... G02F 1/335
                                                      359/305
5,073,685 A * 12/1991 Kobayashi ............ G06F 3/0433
                                                      178/19.02
(Continued)

FOREIGN PATENT DOCUMENTS

JP    H04-317641    11/1992
JP    2003-339696   12/2003
(Continued)

OTHER PUBLICATIONS

H. Taki et al., "Medical Acoustic Imaging Method for Small Calculi Detection Using Correlation Between Ultrasonic Echo Signals with a Filter", *Spring Meeting of Acoustic Society of Japan*, pp. 1249-1250 (Mar. 2009) (in Japanese; see above for relevance).

(Continued)

*Primary Examiner* — Elias Desta
(74) *Attorney, Agent, or Firm* — Fitzpatrick, Cella, Harper & Scinto

(57) ABSTRACT

Provided is a signal processing apparatus including: a transducer that performs scanning through the interior of an object and acquires received waveform data of a plurality of scanlines; an intensity screening unit that outputs a high intensity position at which signal intensity calculated from the received waveform data is higher than a first predetermined value; a correlation calculation unit that calculates a correlation value in a constant-width division for received waveform data of a first scanline and of a second scanline having a predetermined correlation with the first scanline; a position extraction unit that extracts, as a candidate position of a singular region, a position which corresponds to a high intensity position and for which the correlation value is lower than a second predetermined value; and an image processor that performs signal processing of generating image data of the object on the basis of the received waveform data.

15 Claims, 16 Drawing Sheets

(51) Int. Cl.
  *A61B 8/14* (2006.01)
  *A61B 8/00* (2006.01)
  *A61B 8/08* (2006.01)
  *G01S 7/52* (2006.01)
  *G01S 15/89* (2006.01)

(52) U.S. Cl.
  CPC ......... *A61B 8/5207* (2013.01); *G01S 7/52036* (2013.01); *G01S 7/52073* (2013.01); *G01S 15/8977* (2013.01)

(56) References Cited

U.S. PATENT DOCUMENTS

| | | | |
|---|---|---|---|
| 5,309,914 A | 5/1994 | Iinuma | 128/660.07 |
| 8,784,317 B2 * | 7/2014 | Taki | A61B 8/0833 382/128 |
| 2011/0083511 A1 | 4/2011 | Taki et al. | 73/602 |
| 2011/0307181 A1 | 12/2011 | Nagae | 702/19 |
| 2012/0259198 A1 | 10/2012 | Nagae et al. | 600/407 |
| 2012/0314534 A1 | 12/2012 | Yoda et al. | 367/7 |
| 2014/0051970 A1 | 2/2014 | Ebisawa et al. | 600/407 |
| 2014/0056105 A1 | 2/2014 | Nagae et al. | 367/87 |

FOREIGN PATENT DOCUMENTS

| | | |
|---|---|---|
| JP | 2005-169155 | 6/2005 |
| JP | 2010-051782 | 3/2010 |
| WO | 2006/044996 | 4/2006 |
| WO | 2010/013792 | 2/2010 |

OTHER PUBLICATIONS

H. Taki et al., "Small Calculus Detection for Medical Acoustic Imaging Using Cross-Correlation between Echo Signals", 2009 *IEEE International Ultrasonics Symposium Proceedings*, pp. 2398-2401 (2009).

G. Hayward et al., "Low Power Ultrasonic Imaging using Digital Correlation", *Ultrasonics* vol. 27, pp. 288-296 (Sep. 1989).

E. Santos Filho et al., "A System for Tissue Characterization and Quantification of Calcium Regions in Intravascular Ultrasound", *2006 IEEE Ultrasonics Symposium*, pp. 1294-1297 (2006).

JPO Office Action issued on Oct. 21, 2014 in counterpart Jap[anise patent application 2011-022776, with translation.

* cited by examiner

SIGNAL PROCESSING APPARATUS

TECHNICAL FIELD

The present invention relates to a signal processing apparatus and ultrasound device that acquire tomographic images or three-dimensional images of a sample using ultrasound waves that are elastic waves, and more particularly, to a signal processing apparatus and ultrasound device that detect a singular region such as a high-reflection body.

BACKGROUND ART

Conventional devices that are capable of obtaining tomographic images using ultrasound waves, which are ordinary elastic waves, have a transmission unit for transmitting ultrasound waves, which are elastic waves, to a sample, a reception unit for receiving reflected waves, and scanning means for scanning transmission and reception waves. There is also provided means for converting the received reflection signals to brightness signals, and visualizing the signals. The interior of a sample is thus observed using a time-series tomographic image obtained by way of the above means. In one form of the above device, the abovementioned scanning means scans ultrasound waves, up and down, left and right, as a result of which a three-dimensional image can be obtained.

Living organisms are one example of subjects that can be examined by ultrasound waves. Ultrasound waves are advantageous in terms of, for instance, real-time characteristics, simplicity and non-invasiveness, and are thus widely used for observing the interior of organisms.

Ultrasound waves that are used for in-vivo observation are transmitted and received by way of a plurality of electromechanical transducer elements (mainly piezoelectric elements, capacitive ultrasound transducer elements and the like).

During transmission, ultrasound waves are generated, converging at a focus position, through application of an electric signal to a plurality of elements, in a time-staggered fashion, in such a manner that the phases of the ultrasound waves coincide at the focus position. The region traversed by ultrasound waves generated according to such driving is centered about a straight line that joins the focus position and the central positions of the plurality of elements that are driven. A transmission beam is formed so as to pass through this region. During reception, the time delays corresponding to the focus position are corrected and added, for the electric signals generated in the plurality of elements on the basis of the received ultrasound waves. Reflected signals of the ultrasound waves at the focus position are acquired as a result. Adding electric signals from the plurality of elements yields waveform data that holds a waveform of the ultrasound waves. An envelope of the received waveform data is acquired next (this is also referred to as environment detection), whereby the received waveform data is converted to intensity data. Lastly, this intensity data is thinned and/or rounded, in accordance with the pixels of the image on which the intensity data is to be displayed, followed by interpolation, as the case may require, to form an image thereby. The focus position during reception can be modified in real time. The region in the focus position as generated in the reception process for the transmission beam constitutes a region that is traversed by the reception beam.

In an ultrasound diagnosis apparatus, controlling transmission and reception in such a way enables transmission of ultrasound waves to a portion that is to be observed, reception of resulting reflected waves, and imaging of the interior of the organism. The straight-line regions acquired based on the transmission beams and the reception beams are called scanlines. An image is formed by arranging a plurality of scanline data.

Ultrasound waves generated according to the above principles enable non-invasive imaging of the interior of an organism, and hence ultrasound waves are widely used for detecting various situations in a body. One such instance is the detection of high-reflection bodies, such as calculi or the like. A widely practiced method for detecting calculi in medical facilities involves detecting the presence of calculi depending on whether an acoustic shadow appears on images of deeper sites behind a calculus, i.e. on a farther side from the probe. An acoustic shadow is a shadow portion that arises through failing of an image to be formed behind a high-reflection body, since the ultrasound pulse does not reach behind the high-reflection body, while the reception beam is blocked by the high-reflection body.

Patent Literature 1 (PTL 1) discloses an ultrasound device in which a correlation between adjacent scanlines is acquired, in order to set scanline density, and a transmission beamformer or reception beamformer is controlled depending on the result.

Patent Literature 2 (PTL 2) discloses an ultrasound device in which tissue contours are extracted on the basis of image data.

Patent Literature 3 (PTL 3) discloses a signal processing apparatus wherein there is acquired received waveform data of a plurality of scanlines through scanning of an elastic wave beam through the interior of an object, and wherein signal processing is performed in order to form a tomographic image of the object on the basis of received waveform data of the plurality of scanlines, the apparatus comprising: an inter-scanline correlation calculation unit that calculates a correlation value of received waveform data between a first scanline and a second scanline having a predetermined correlation with the first scanline, for each of a plurality of positions on the scanline; and a correlation change position extraction unit that extracts, from among the plurality of positions on the scanline, a position at which a singular region is likely to be present, in the form of a position at which the correlation value takes on a value that differs from a predetermined value.

Patent Literature 4 (PTL 4) discloses an ultrasound imaging apparatus in which linear boundaries in tomographic images, or boundary surfaces in three-dimensional information, are detected by using phase information of reflected waves. Patent Literature 4 (PTL 4) discloses specific means that involves displaying contour information in an object, as well as boundaries contiguous to an object, by obtaining a time at which a cross-correlation function between scanlines is maximal, from designated positions, and by linking positions that are obtained on the basis of the obtained times.

Non-Patent Literature 1 (NPL 1) discloses a method that involves obtaining correlation values between adjacent scanlines, and extracting calculus positions on the basis of changes in the correlation values for a same depth. Non-Patent Literature 1 (NPL 1) discloses also a method for enhancing positional precision upon calculus extraction by applying a pattern matching method to changes in correlation values for a same depth.

CITATION LIST

Patent Literature

PTL 1: Japanese Patent Application Laid-open No. 2003-339696

PTL 2: Japanese Patent Application Laid-open No. 2005-169155

PTL 3: Japanese Patent Application Laid-open No. 2010-051782

PTL 4: Japanese Patent Application Laid-open No. H4-317641

Non Patent Literature

NPL 1: Hirofumi Taki, Tetsuya Matsuda and Toru Sato, "Medical acoustic imaging method for small calculi detection using correlation between ultrasonic echo signals with a filter", Spring Meeting of Acoustic Society of Japan, pp. 1249-1250, 2009.

SUMMARY OF INVENTION

Technical Problem

However, the above-described acoustic shadows fail to form readily in some cases, depending on the position, size and shape of the high-reflection body, and it becomes then difficult to extract the high-reflection body. One such case is found in techniques that involve shifting the focus position, in real time, during reception, as described above. In such a technique, the reception beam can be narrowed at all depths of the target to be observed. This is effective for enhancing, as a result, the resolution of the image as a whole.

This is explained with reference to FIG. 1. In FIG. 1, the reference numeral 100 denotes a high-reflection body, 101 denotes a reception focus and 102 denotes a reception beam. In a case where, for instance, the reception focus 101 is set to a deeper position than that of the high-reflection body 100, the width of the reception beam 102 spreads widely at the depth at which the high-reflection body is present; as a result, there are received ultrasound waves that slip past the high-reflection body. In consequence, the acoustic shadow derived from the high-reflection body 100 does not form easily, and searching for acoustic shadows becomes difficult. Also, the intensity of the reflected wave (also referred to as reflection echo or reflection signal) in the beam that is focused onto the high-reflection body may be low, depending on the size and the shape of the high-reflection body. For instance, the intensity of reflected waves as detected by a detector is small when the high-reflection body is of small size (for instance, in case of a diameter of 1 mm or less in an approximation where the high-reflection body has a spherical shape). The reflected wave intensity detected by the detector is likewise small in cases where a reflective surface of highest reflectance and having a nonuniform shape (for instance, partially planar or concavo-convex shape, non-symmetrical shape and the like) is absent on the side of the detector. That is, the detection signal may be weak even for a high-reflection body. In such cases, the difference between the signal intensities of reflected waves obtained at the position at which the high-reflection body is present and at the periphery thereof is small.

As mentioned above, the final image data is obtained after subjecting the ultrasound signals received for each element to the following processes. Specifically, (1) received waveform data is obtained through time delay correction and an addition process; (2) intensity data is obtained by envelope acquisition; and (3) intensity data is subjected to thinning, rounding and interpolation, to yield image data. However, much information from the ultrasound signals may become lost in the course of such processes. In some cases, for instance, the reflection echo intensity from the high-reflection body is comparable to the reflection echo intensity from planar-like tissue interfaces. Also, the reflection echo from a high-reflection body may be buried, in the image, in the reflection echo from tissue interfaces.

FIG. 2 to FIG. 4 are diagrams illustrating schematically such instances. FIG. 2 illustrates an instance where a high-reflection body 104 is disposed in a simulated tissue 103. An ultrasound probe 001 is disposed on the top face of the simulated tissue 103, and ultrasound waves are transmitted and received.

FIG. 3 is a graph of the plotted reflection echo intensities from depths A-A', B-B', and C-C' in FIG. 2. In the graph of FIG. 3, the high-reflection body is disposed in the vicinity of the center of the horizontal axis. As the graph shows, the echo from the high-reflection body stands out from the reflection echo of surrounding tissue.

FIG. 4 illustrates simulated tissue 103 inside which there is arranged a layer-like tissue 105, but no high-reflection body. The reflectance of the layer-like tissue 105 is set to be lower than that of the high-reflection body. FIG. 3 illustrates superposed graphs resulting from schematically plotting reflection echo intensities from depths A-A', B-B', and C-C' in FIG. 4. In the graph of FIG. 3, the solid lined denoted by the legend "high-reflection body A-A'" is a plot of reflection echo intensity from a high-reflection body, as explained above. As the graph shows, the reflection echo intensity from the layer-like tissue having low reflectance is nonetheless comparable to the reflection echo intensity of the high-reflection body having high reflectance. Thus, it is difficult to determine whether a high-reflection body is present or not on the basis of reflection echo intensity alone. That is, signals having some intensity may be detected in certain cases, even in the absence of a high-reflection body.

In cases where a spectral pattern arises on account of interference with reflection echo from small scattering bodies, and the reflection echo from a high-reflection body becomes mixed therein, it is difficult to selectively extract signals arising only from the small scattering bodies, and to discriminate those signals from other signals. High-reflection bodies are difficult to discriminate, in particular, if the high-reflection body appears on the image in the form of small, point-like echo.

The ultrasound imaging apparatus disclosed in PTL 4 is a device in which positions, from designated positions, are obtained that have a time lag for which an inter-scanline cross-correlation function is maximal, and the positions are linked, to display a boundary as a result. Therefore, when a high-reflection body is present in the form of point-like echo (when no echo is detected on adjacent scanlines), other positions that should be linked to this point-like echo are absent (i.e. there is only the point of the high-reflection body position). Therefore, it is difficult to extract high-reflection bodies by relying on the method disclosed in PTL 4.

To determine the presence or absence of a high-reflection body and to extract position information in such cases, a high-sensitivity technique is needed that gives greater consideration to the special characteristics of high-reflection bodies, rather than by using image data.

The calculus position extraction technology disclosed in NPL 1 involves extracting calculus positions by using correlation values of positions at a same depth. This technology could conceivably be used for depths where calculi are absent and reflected ultrasound waves are few. In such a case, the SN ratio of the signal is low, since reflected ultrasound waves are few, and there is the chance that a low adjacent cross-correlation between scan lines may be calculated, even for regions where calculi are absent. This may lower the precision of calculus position extraction, and give rise to unstable position extraction results.

In the light of the above, it is an object of the present invention to provide a technology that allows detecting, stably and with good precision, positions at which a singular region is likely to be present, for instance a high-reflection body, in particular a small high-reflection body, on the basis of respective received waveform data of elastic waves.

Solution to Problem

This invention provides a signal processing apparatus, comprising:

an transducer that scans an elastic wave beam through an interior of an object and acquires received waveform data of a plurality of scanlines;

an intensity screening unit that calculates signal intensities on the basis of the received waveform data of the plurality of scanlines, and outputs, as a high intensity position, a position at which a calculated signal intensity is higher than a first predetermined value;

a correlation calculation unit that selects, from among the plurality of scanlines, a first scanline and a second scanline having a predetermined correlation with the first scanline, and that calculates a correlation value between received waveform data of the first scanline and the second scanline, at a plurality of constant-width divisions;

a position extraction unit that extracts, as a candidate position at which a singular region is likely to be present, a position corresponding to the high intensity position outputted by the intensity screening unit, at a division where the correlation value is lower than a second predetermined value; and an image processing unit that performs signal processing for generating image data of the object from the received waveform data of the plurality of scanlines.

Advantageous Effects of Invention

The present invention allows detecting, stably and with good precision, positions that may be a singular region, for instance a high-reflection body, in particular a small high-reflection body, on the basis of received waveform data of elastic waves.

Further features of the present invention will become apparent from the following description of exemplary embodiments with reference to the attached drawings.

DESCRIPTION OF EMBODIMENTS

Figure 1:
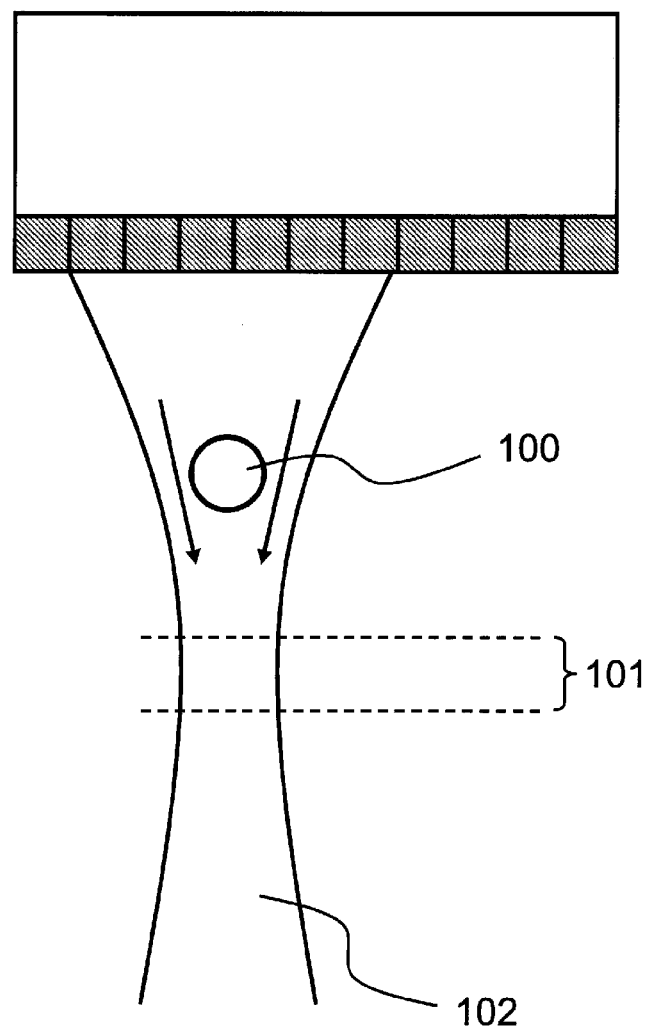
FIG. 1 is a diagram for explaining the spread of a reception beam width.
Figure 2:
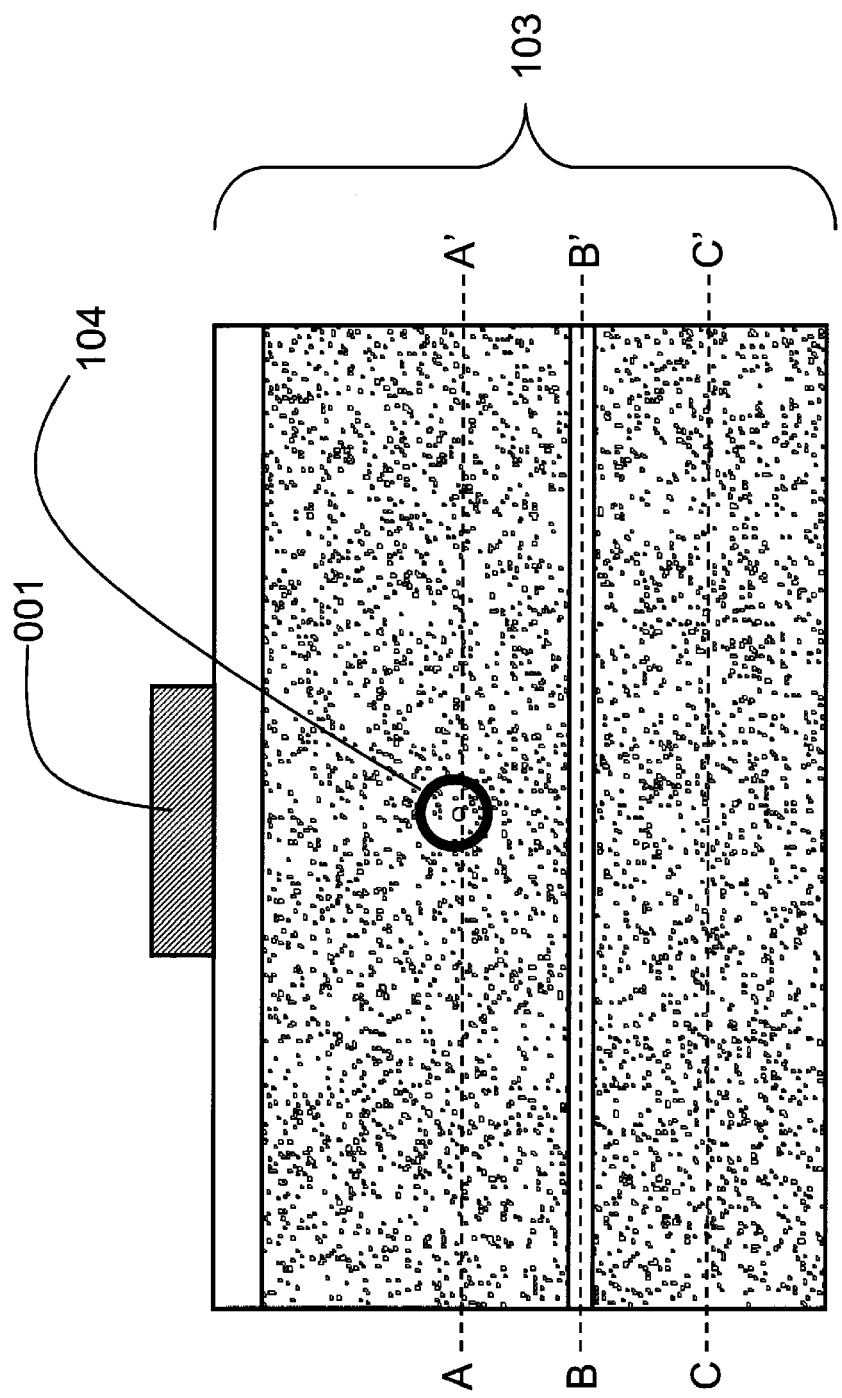
FIG. 2 is a diagram illustrating a pseudo-tissue model in which a high-reflection body is present.
Figure 3:
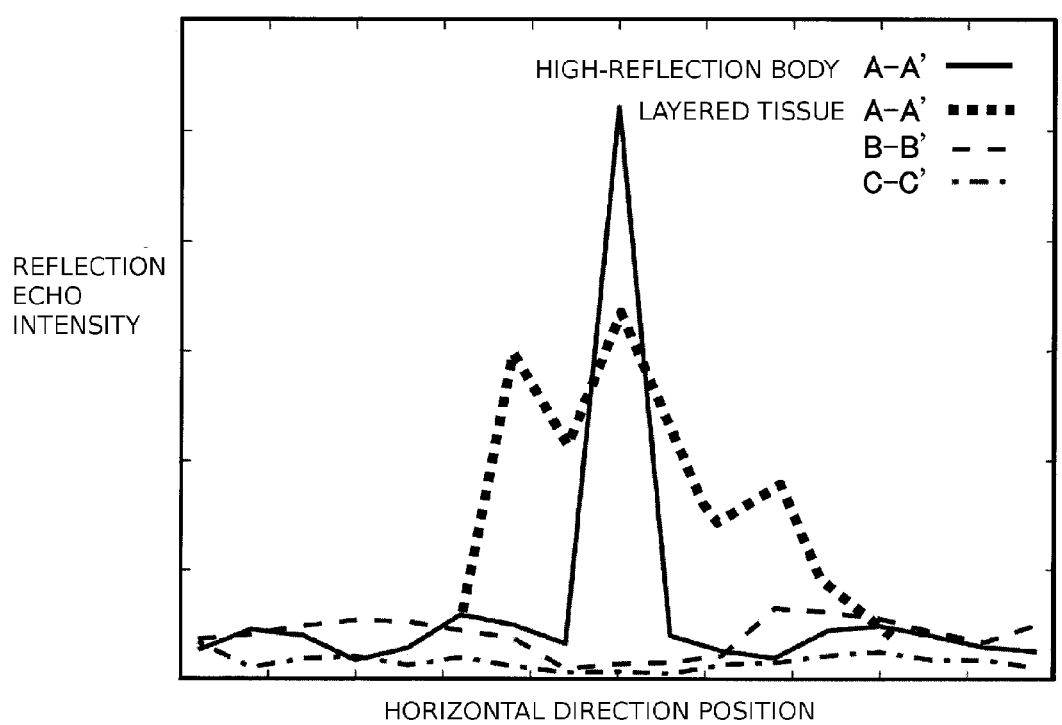
FIG. 3 is a diagram illustrating reflection echo intensity in an instance where a high-reflection body is present.
Figure 4:
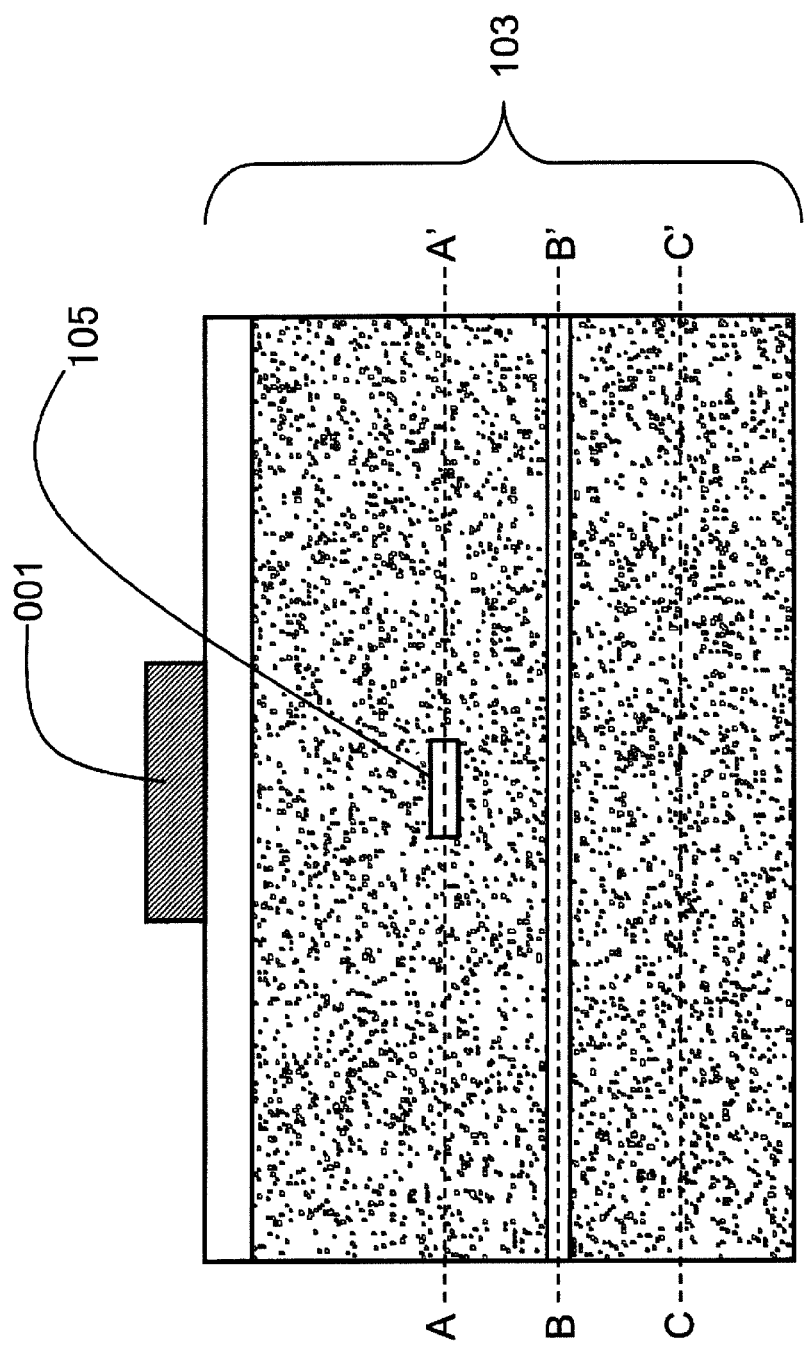
FIG. 4 is a diagram illustrating a pseudo-tissue model in which layer-like tissue is present.

In the present invention, the term elastic wave denotes a vibrational wave such as an ultrasound wave.

In the present invention, the term singular region denotes a region, inside an object, such that the state of the region is different from that of the surroundings. For instance, the singular region is a region having layered tissue, or a region that constitutes a high-reflection body to ultrasound waves, typically as a result of calcification or the like, i.e. regions whose tissues, structure, characteristics and so forth are dissimilar from those of the surroundings.

In the present invention, the size of a small high-reflection body as one target for detection refers to a diameter of 2 mm or less, in a case where the high-reflection body is spherical in an approximation. The size of a small high-reflection body refers to a size of 1 mm or less, in particular 100 μm or less. If the diameter of the sphere is 2 mm or less in an approximation where the small high-reflection body is spherical, the reflected waves themselves are difficult to detect, due to their small size, or the signal of the reflected waves is difficult to discriminate from signals of the surroundings.

In the present invention, the term signal intensity denotes an amplitude obtained from an envelope of the received waveform data.

In the present invention, the presence or absence of a high-reflection body is detected by extracting a position at which there drops a cross-correlation between scan lines (cross-correlation value) that is calculated at a constant-width division that encompasses a position at which signal intensity is high. Calculation of correlation values using signals having low SN ratio can be avoided by using data of a division that encompasses thus portions of high signal intensity. Accordingly, this allows obtaining cross-correlation between scan lines with good precision, and allows stably extracting positions at which correlation values decrease.

Small high-reflection bodies can be detected by using data of scanlines that have a mutual correlation value that is equal to or greater than a given value at a region where no high-reflection body is present. Findings by the inventors have shown that high-reflection bodies can be detected between scanlines having, for instance, a cross-correlation of about 0.5.

Preferably, scanlines having yet higher cross-correlation are used in order to enhance the precision in high-reflection body detection. For instance, two scanlines that stand close to each other, or two adjacent scanlines, may yield high cross-correlation scanlines.

In the present invention, the relationship between a first scanline and a second scanline for which the above cross-correlation is to be calculated denotes a relationship that satisfies the condition below. Specifically, the relationship is a relationship such that the correlation value between the first scanline and the second scanline is 0.5 or greater between the first scanline and the second scanline at a region at which no high-reflection body is present in the object. In the present invention, preferably, the correlation value is 0.7 or greater, and optimally 0.9 or greater.

The correlation value between the first scanline and the second scanline is explained next. A correlation value of 1.0 between the first scanline and the second scanline indicates that the first scanline and the second scanline are the same wave (signal). A correlation value of 0 between the first scanline and the second scanline means that the first scanline and the second scanline are waves (signals) of significantly (typically, completely) different size. The higher the correlation values between scanlines, the more similar are the states of acoustic impedance distribution at the region at which the reflected waves (reflection echo) are formed. In imaging using ultrasound waves, the correlation values exhibit a constant value if there are regions at which adjacent scanlines overlap within the beam width range. Preferably, therefore, a beam is transmitted at such a beam spacing as allows obtaining overlapping regions within the beam width range.

In the present invention there can be obtained a significant difference between the correlation value (correlation value before reflection by the high-reflection body) and a correlation value between the first scanline and the second scanline at a position that is deeper than the position of the high-reflection body, in a case where the correlation value is 0.5 or greater, and one scanline is reflected by a high-reflection body.

The present invention allows distinguishing between a layered tissue and a high-reflection body (in particular, a small calcification or the like) as a reflecting body having a given reflectance, within the object. Large high-reflection bodies can be distinguished also by conventional methods, since regions of substantial reflection are large in size.

The present invention allows specifying the position at which a high-reflection body or layered tissue is likely to be present on the basis of changes in correlation values between close or adjacent scan lines. In the case of a (small) high-reflection body, only one of two close or adjacent scanlines passes through the position of the (small) high-reflection body) while the other scanline does not traverse the position of the high-reflection body. When transmitted ultrasound waves traverse the position of the high-reflection body, the ultrasound waves are reflected by the high-reflection body or pass through the high-reflection body. The Born approximation applies to ultrasound waves inside ordinary organisms, and waveforms are attenuated without distortion. However, waveforms are distorted by the high-reflection body, on account of, for instance, formation of creeping waves, presence of sound-speed slow waves that traverse the high-reflection body, as well as diffraction and multiple reflection in the high-reflection body and the like. Therefore, the waveforms of ultrasound waves that pass through the position of the high-reflection body and the waveforms of ultrasound waves that do not pass through the position of the high-reflection body exhibit variations, and correction values are lower. By contrast, correlation values virtually do not change, and there occurs no waveform distortion, in a case where the ultrasound waves pass through the position of layered tissue, since the Born approximation applies in that case.

In the present invention, thus, it becomes possible to distinguish between a high-reflection body, for which the correlation value between two close or adjacent scanlines decreases, from a layered tissue, for which the correlation value does not change, or is small, taking as a reference a position at which a high-reflection body or layered tissue is present. As the case may require, the signal processing apparatus or ultrasound device of the present invention may be provided with a discrimination unit that discriminates between a high-reflection body and a layered tissue on the basis of the above-described discrimination method.

Findings by the inventors have revealed that, preferably, the mutual correlation between the first scanline and the second scanline is preferably strong (large), and that, typically, two adjacent scanlines are preferable. If a relationship between the correlation values is satisfied, however, the first scanline and the second scanline need not necessarily be adjacent, and other scanlines may be interposed between the foregoing scanlines. Thus, two close scanlines may be used, so long as the above-described relationship is satisfied.

Figure 5:
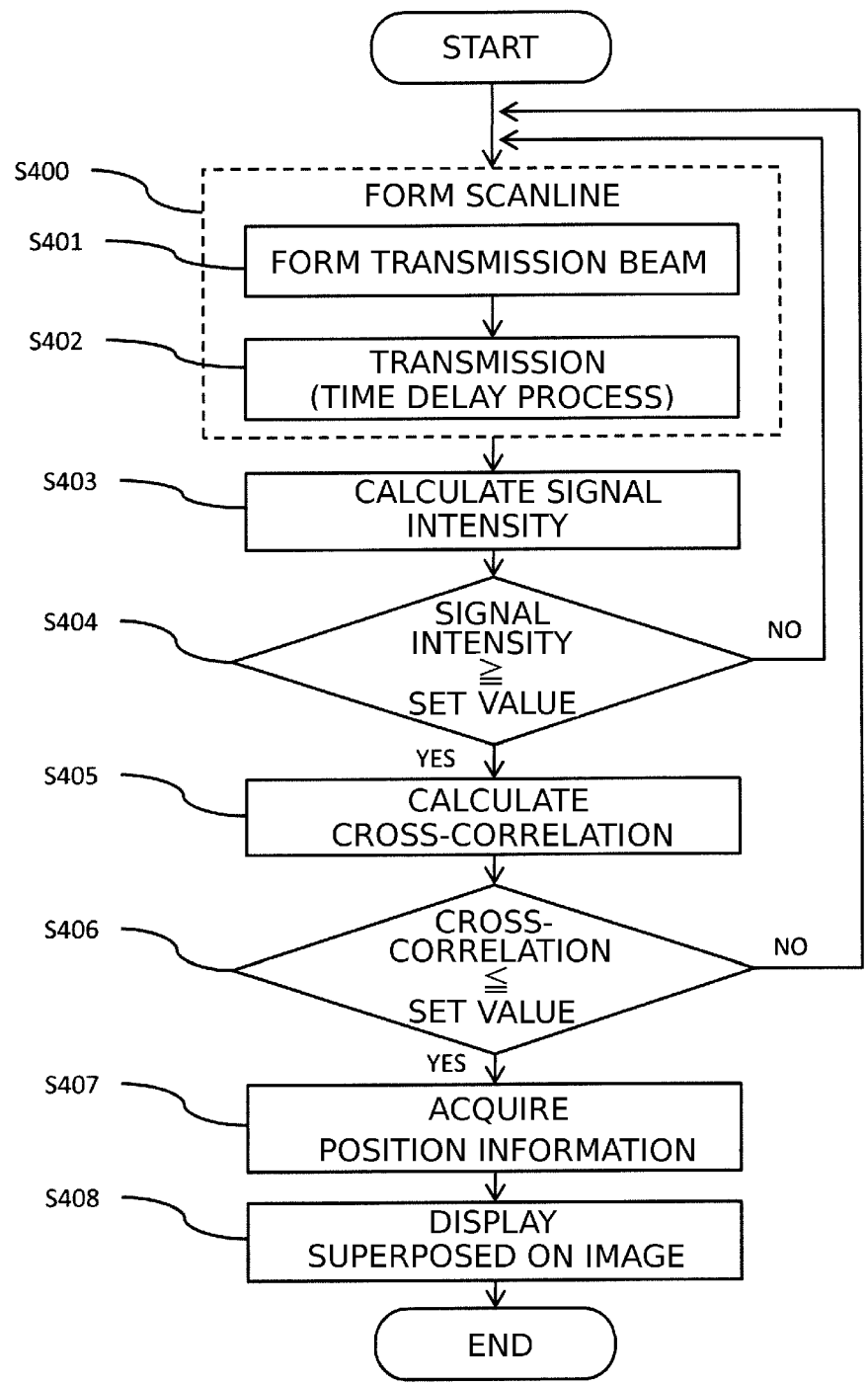
FIG. 5 is an example of a flowchart denoting a candidate position.

FIG. 5 illustrates a flowchart for explaining a procedure for obtaining a candidate position of a high-reflection body in the present invention.

A premise for scanline formation (S400) mandates a correlation value of 0.5 or greater between a first scanline and a second scanline in a region at which there is no high-reflection body. Next, a transmission beam that satisfies the above condition is formed, and is transmitted to the object (S401). Reflected waves from a specific position within the object are received (S402). The signal intensity of reception waveforms is calculated (S403), and is compared with a set value that is set beforehand (S404). If the comparison result does not satisfy a predetermined condition, there is formed a subsequent scanline. If the comparison result of signal intensity satisfies a predetermined condition, a correlation value is calculated (S405) and is compared with a set value that is set beforehand (S406). If the comparison result satisfies a predetermined condition, position information is acquired (S407). If the comparison result does not satisfy a predetermined condition, the process returns to (S400) and there is formed a subsequent scanline. In the process of S407, position information is acquired and, thereafter, the information is superposed onto the image (S408).

The above procedure is merely an example, and the present invention is not limited to that procedure. For instance, the order of signal intensity calculation (S403) and comparison (S404), and the order of correlation value calculation (S405) and comparison (S406), may be swapped.

Preferred embodiments of the present invention are explained illustratively in detail next with reference to accompanying drawings. A device and method are explained in which ultrasound waves are used as the elastic waves.

Embodiment 1

In Embodiment 1 below there is explained an ultrasound device that calculates a cross-correlation between adjacent scanlines of a region that encompasses a position of high signal intensity, so that the device yields information on a position for which a correlation is equal to or smaller than a set value.

Figure 6:
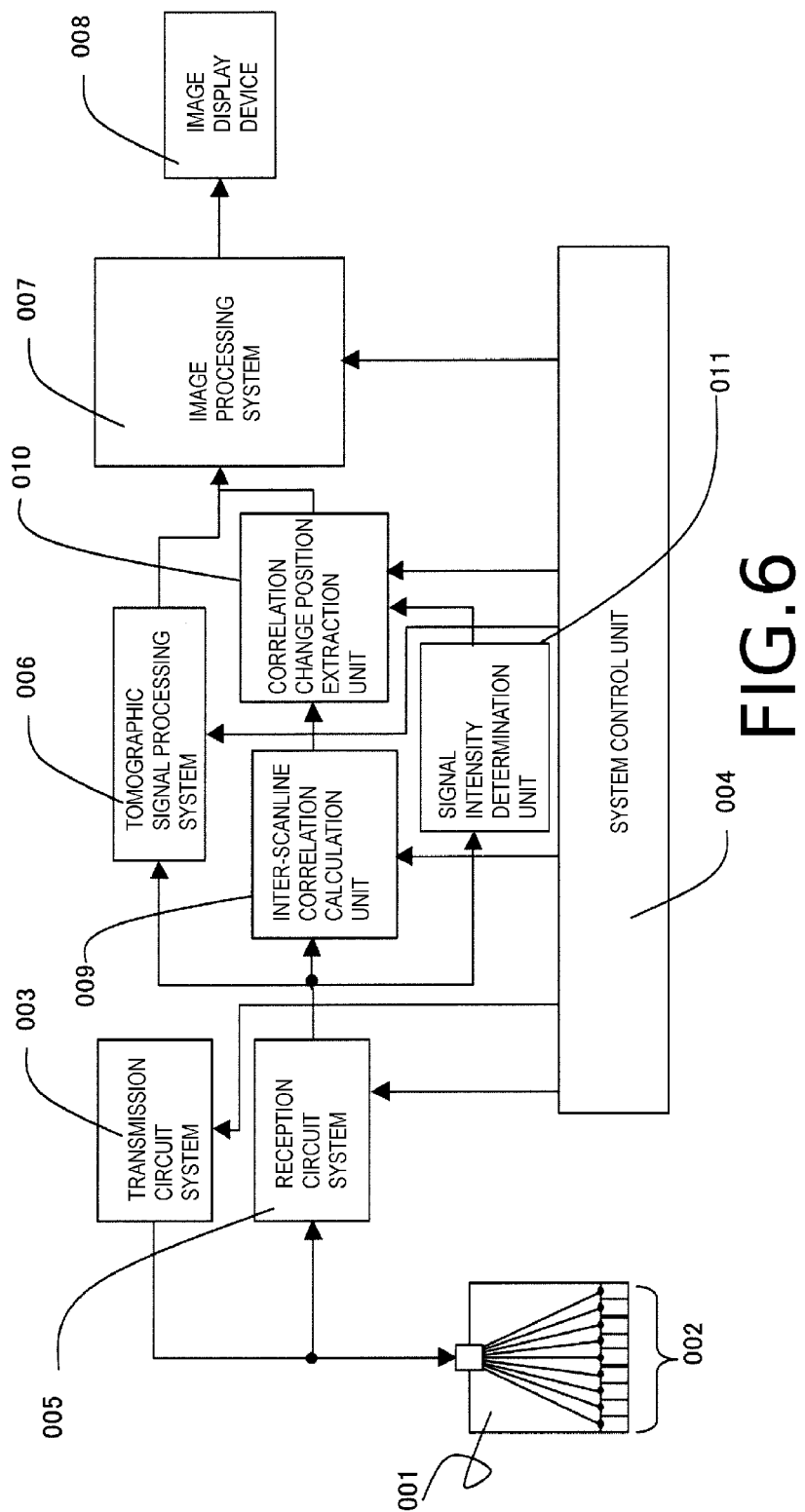
FIG. 6 is a block diagram of an ultrasound device of Embodiment 1 of the present invention.

FIG. 6 is a system schematic diagram of an ultrasound device according to Embodiment 1 of the present invention. The ultrasound device has a function for generating and displaying ordinary ultrasound tomographic image data, and a function for detecting a high-reflection body in an organism, and displaying a candidate of the position at which the high-reflection body is present (inter-scanline correlation calculation unit 009, correlation change position extraction unit 010, signal intensity screening unit 011). The latter function is used, for instance, for detecting of regions of calculi and microcalcifications.

(Generation and Display of Tomographic Images)

The flow up to display of a tomographic image will be explained first with reference to FIG. 6. The ultrasound device of the present embodiment is a system to which there is connected an ultrasound probe 001 having a plurality of transducer 002. Once the position of ultrasound transmission (transmission focus is set), a system control unit 004 sends that setting information to a transmission circuit system 003. On the basis of that information, the transmission circuit system 003 determines a time delay and intensity, and transmits an electric signal for driving the plurality of transducer 002 in the ultrasound probe 001. The electric signal is converted to displacement in the transducer 002, and propagates in the form of ultrasound waves through the interior of the object. The ultrasound waves thus transmitted form a linear sound pressure distribution, within the object, that is referred to as a transmission beam. The ultrasound waves that propagate in the object are scattered and reflected according to the acoustic properties of the object, and return, in the form of echo, to the transducer 002. This echo is converted, by the transducer 002, to electric signals that are inputted to a reception circuit system 005. In the reception circuit system 005, a time delay amount is calculated on the basis of information relating to a reception focus position as supplied by the system control unit 004, a time delay process is performed on the inputted time-series electric signals, and the results are added thereafter. This process allows selectively extracting reflected waves (also referred to as reflection echo) at the reception focus position in the object. A region having reception sensitivity as formed according to such a process is referred to as a reception beam for a transmission beam.

The reception circuit system 005 sends the time-series received waveform data thus obtained to a tomographic signal processing system 006. In the tomographic signal processing system 006, the inputted time-series received waveform data is subjected, as the case may require, filtering processing such as bandpass filtering, followed by detection of data envelope and output of the envelope as intensity data. The intensity data is transmitted to an image processing system (image processing unit) 007. The image processing system 007 performs thinning, rounding or interpolation, on data according to the pixels of a display image, using intensity data and position information, of the reception beam and the transmission beam, as sent by the system control unit 004, and generates a brightness signal for each position within an observation region. This series of operations results in the formation of an image for one scanline. The direction and the position of the transmission beam and the reception beam are changed, and a similar process is performed again, to form a scanline of a different region in the object. A plurality of scanlines within the observation region is thus formed, so that, as a result, image data can be generated in the form of tomographic image data of the observation region. The image processing system 007 transmits the tomographic image thus obtained to an image display device 008 for display.

An example has been explained herein in which scanlines are formed by one transmission beam and one reception beam. However, the present invention is not limited thereto, and there can be used also image methods for forming simultaneously a plurality of scanlines through formation of a plurality of reception beams in each transmission. The present invention is not limited to a two-dimensional tomographic image, and may also be used in instances where a three-dimensional region is generated as image data.

(Detection and Display of High-Reflection Bodies)

An explanation follows next, with reference to FIG. 6 through FIG. 9, on a process for detecting a high-reflection body and for display of a candidate of the position at which the high-reflection body is present.

As illustrated in FIG. 6, the ultrasound device comprises the inter-scanline correlation calculation unit 009, the correlation change position extraction unit 010, and the signal intensity screening unit 011. Time-series received waveform data generated by the reception circuit system 005 is sent to the inter-scanline correlation calculation unit 009 and the signal intensity screening unit 011. The inter-scanline correlation calculation unit corresponds to a correlation calculation unit of the present invention. The correlation change position extraction unit corresponds to a position extraction unit of the present invention. The signal intensity screening unit corresponds to an intensity screening unit of the present invention.

Figure 7:
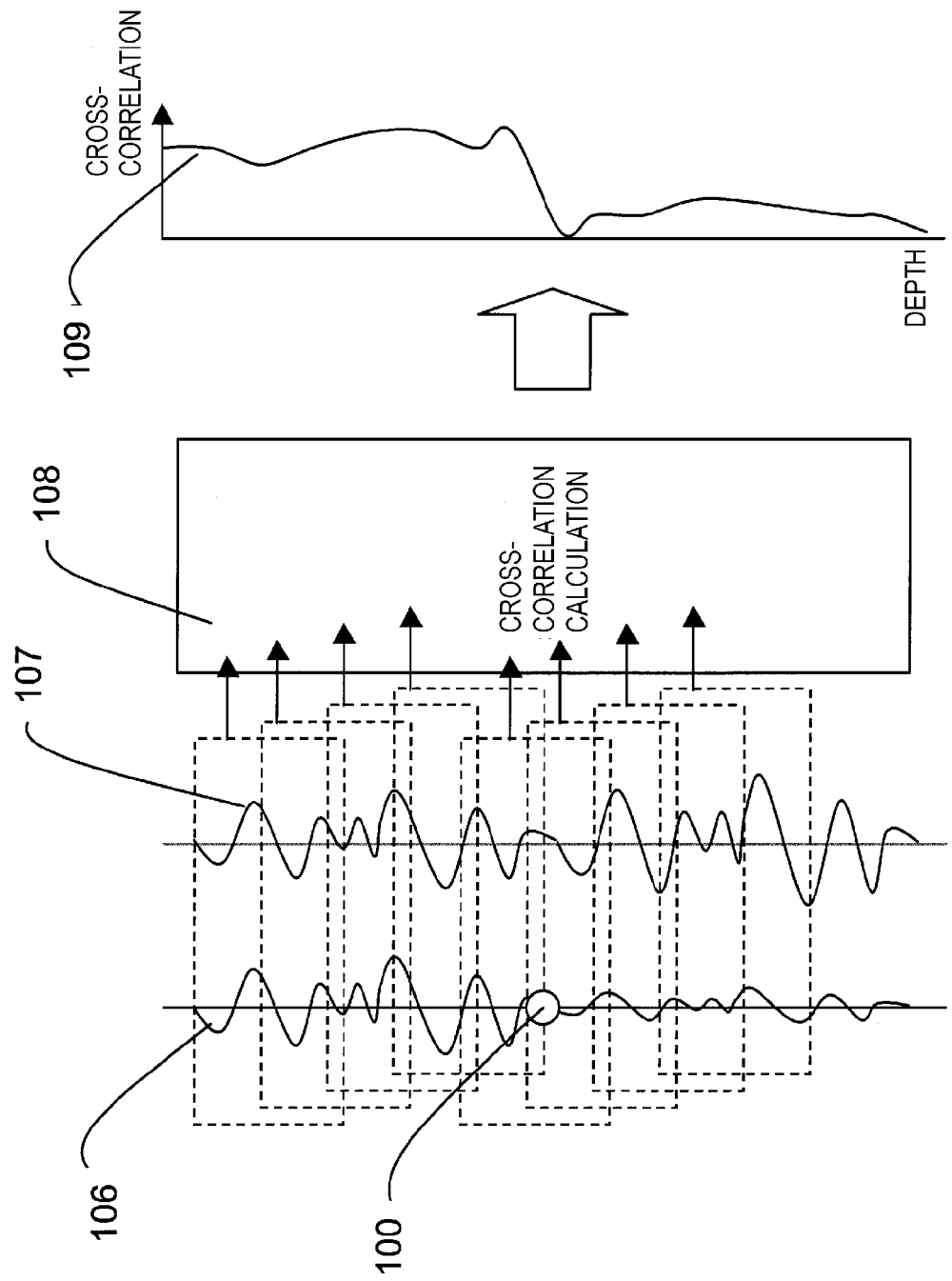
FIG. 7 is a diagram for explaining a procedure for cross-correlation calculation.

The inter-scanline correlation calculation unit 009 calculates a cross-correlation along a time axis of between adjacent scanlines, on the basis of received waveform data and information on scanline position as sent by the system control unit 004. FIG. 7 illustrates a conceptual diagram of the above. Herein, $S_1(r)$ is an analytical expression of received waveform data 106 of a first scanline, and $S_2(r)$ is an analytical expression of received waveform data 107 of an adjacent second scanline. The inter-scanline correlation calculation unit 009 sets a position of interest (depth of interest) on the scanline, and extracts (clips) waveform data of a region having a predetermined width (constant-width division) with reference to the position of interest, on the basis of respective received waveform data. A cross-correlation calculation 108 is performed between the extracted (clipped) received waveform data. This operation yields a correlation value (also referred to as cross-correlation value) of the position of interest. Correlation values for a plurality of positions (depths) on a scanline can be obtained by repeating the above operation while shifting the position of interest in a depth direction (time axis direction, for received waveform data). Graph 109 in FIG. 7 illustrates the change of a correlation value thus obtained in the depth direction. For instance, the correlation value is obtained in the form of a maximum value relating to $\tau$ in $Y(\tau)$ of equation (1).

[Math. 1]

$$Y(\tau) = \frac{\left| \sum_{z'=z_1}^{z_2} S_1(z') S_2(z'+\tau)^* \right|}{\sqrt{\sum_{z'=z_1}^{z_2} |S_1(z')|^2 \sum_{z'=z_1}^{z_2} |S_2(z'+\tau)|^2}} \quad (1)$$

In the equation, $z_1$ denotes the depth of interest (position of interest) and $z_2-z_1$ denotes a division width over which the cross-correlation is acquired. The correlation values at different positions are obtained by modifying the depth of interest $z_1$. Herein, the value of $\tau$ is set to lie within a range from about the wavelength of the ultrasound waves to several tens of times that wavelength.

FIG. 7 illustrates an example of a high-reflection body 100 being present on a first scanline. It is found that a cross-correlation 109 decreases at a position that is deeper than that of the high-reflection body 100.

Figure 8:
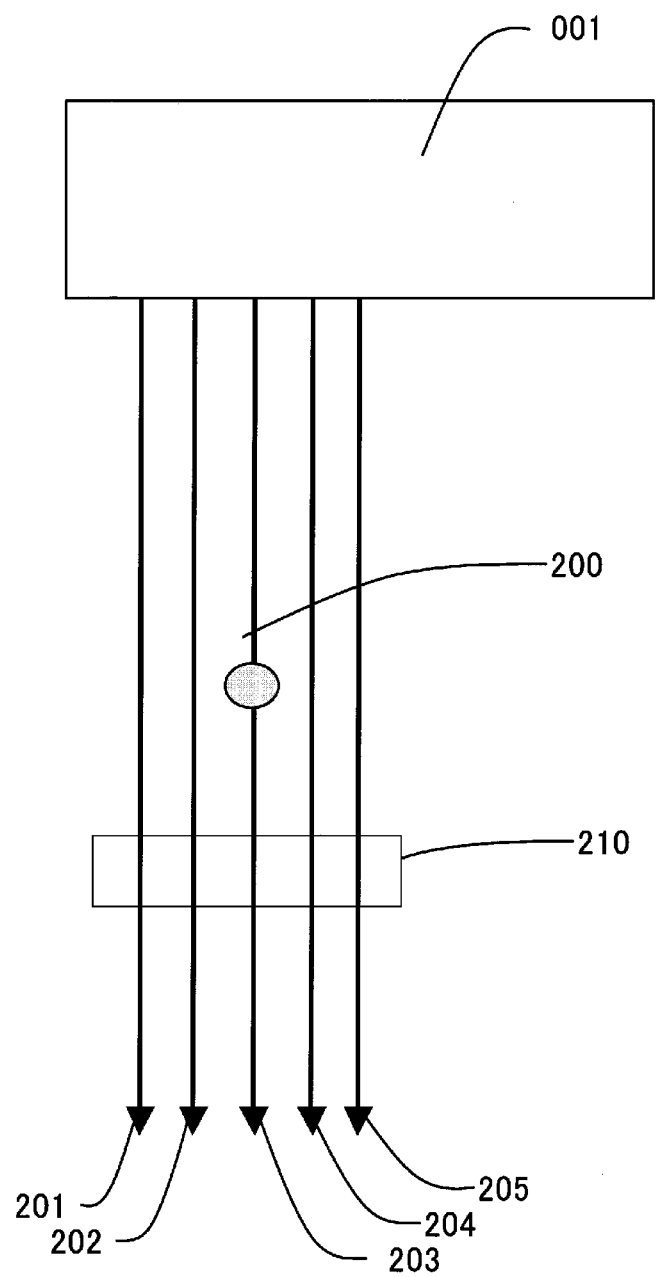
FIG. 8 is a diagram for explaining adjacent scanlines.

Adjacent scanlines are explained with reference to FIG. 8. FIG. 8 is a diagram illustrating schematically the ultrasound probe 001, five scanlines 201, 202, 203, 204, 205 formed in the object, a high-reflection body 200, and a layered tissue 210. In a case where, for example, data on scanline 201 is acquired, and data on scanline 202 is acquired thereafter, the inter-scanline correlation calculation unit 009 calculates a cross-correlation between scanlines 201, 202, since scanlines 201, 202 are mutually adjacent. In a case where, for example, the scanline acquisition order is scanline 201, scanline 203, scanline 205, scanline 202 and scanline 204, the adjacent scanline data is acquired for an instance where scanline 202 is acquired first. At this point in time, therefore, the inter-scanline correlation calculation unit 009 calculates a cross-correlation value between scanlines 201, 202.

The inter-scanline correlation calculation unit 009 calculates a cross-correlation of received waveform data of two scanlines along a time axis (along the depth of the object). Adjacent scanlines are set so as to overlap partly at the observation region, and hence high correlation is ordinarily obtained in a case where layered tissue straddles the two scanlines. For instance, the cross-correlation between scanline 204 and scanline 205 has a correlation value that is equal to or greater than a given value at a portion where a layered tissue 210 is present at a deep position in the object. Focusing now on scanline 202 and scanline 203, a high-reflection body 200 is present halfway in scanline 203. As a result, the cross-correlation between scanline 202 and scanline 203 drops at a portion deeper than that of the high-reflection body 200. The inter-scanline correlation calculation unit 009 transmits, to the correlation change position extraction unit 010, correlation values obtained for each site having such properties.

Figure 9:
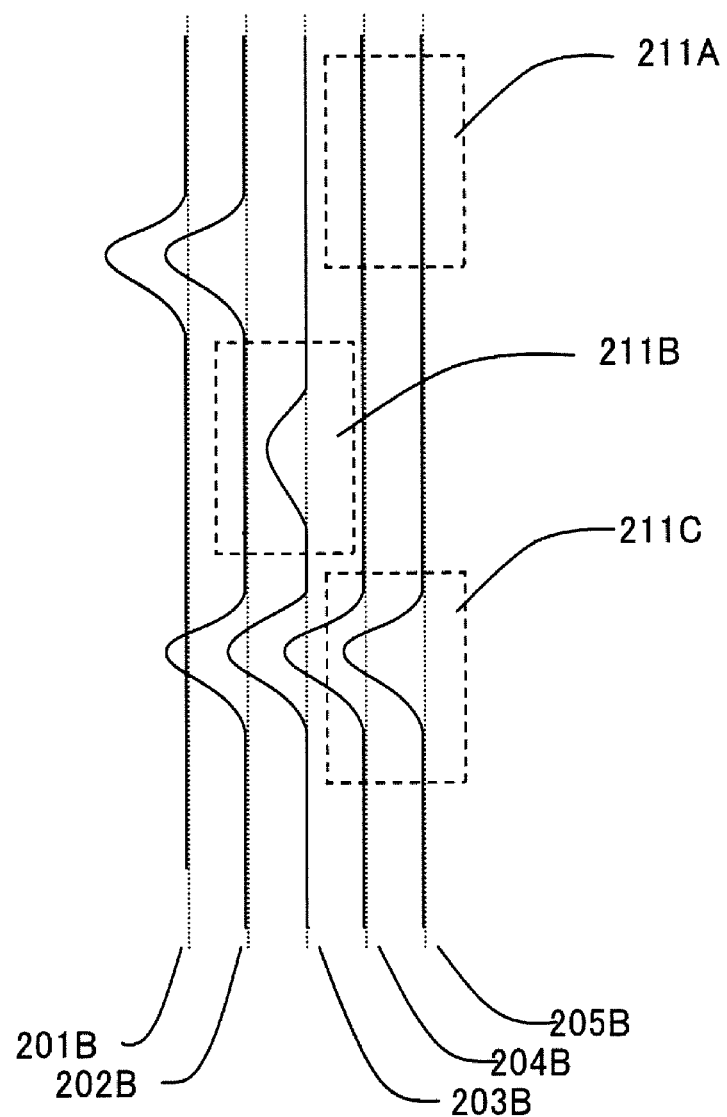
FIG. 9 is a diagram illustrating schematically received signal intensity.

FIG. 9 is a diagram illustrating schematically signal intensities 201B to 205B calculated by the signal intensity screening unit 011 on the basis of transmission and reception of scanlines 201 through 205. Ultrasound waves are reflected at the position of the high-reflection body 200 and the layered tissue 210. Accordingly, signal intensity is large at positions corresponding thereto. The signal intensity screening unit 011 extracts a position at which a high-level signal intensity at a proportion that is determined separately is shown, from among signal intensities in the image capture region, and outputs that position information.

Findings by the inventors have revealed that in images in ordinary ultrasonography the signal intensity of high-reflection bodies such as calculi or the like are found within the top 10%, typically the top 1% in the image capture region. Accordingly, a proportion determined separately (first predetermined value) may be set to, for instance, a value of 10% or 1%, or 0.5% depending on the circumstances. If the proportion is set to be large, it becomes possible to find smaller high-reflection bodies of smaller signal intensity. If the proportion is set to be small, there increases the specificity is position extraction of the high-reflection body.

In FIG. 9, for instance, the signal intensity at region 211B and region 211C is high. Therefore, position information relating to these regions is outputted.

Focusing now on regions 211A, 211B, 211C, a high-reflection body is present at 211B. Therefore, the correlation value between scanline 202 and scanline 203 is lower, as explained above. A layered tissue is present at region 211C, and hence the correlation value between scanline 204 and scanline 205 becomes higher. In region 211A, however, there is no reflecting body, such as layered tissue or the like, and hence the received signal intensity is lower. The SN ratio at such portions of low received signal intensity is poor. Therefore, a low correlation value may be obtained, even between adjacent scanlines, upon calculation of the cross-correlation between scan lines. Low correlation values that occur in such instances may result in loss of precision and of stability in position extraction of the high-reflection body.

The correlation change position extraction unit 010 receives a correlation value for each position, as outputted by the inter-scanline correlation calculation unit 009, as well as position information outputted by the signal intensity screening unit 011. The correlation change position extraction unit 010 extracts only a correlation value for which a position outputted by the signal intensity screening unit 011 is within a correlation window (depth range given by $z_1$ and $z_2$ in the equation for obtaining the correlation value).

The correlation change position extraction unit 010 outputs position information having a correlation value that is lower, by a given amount or greater, than a mean value of the extracted correlation values.

The set of correlation values thus extracted are in a state such that low correlation values, obtained from regions of poor SN ratio, are excluded. As a result, this allows enhancing the precision for which a position having a low correlation value is a position at which a high-reflection body is present, and allows obtaining more stable extraction results.

Figure 10A:
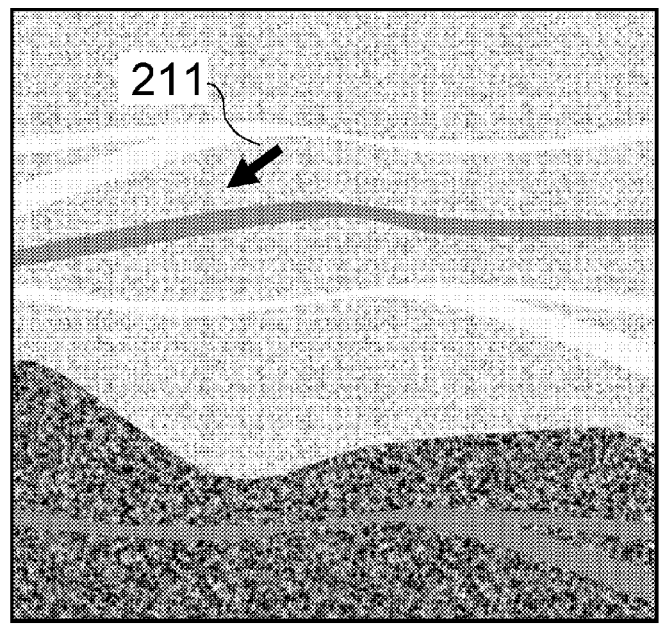
FIG. 10A and FIG. 10B are display examples of tomographic images and position information of a high-reflection body.
Figure 10B:
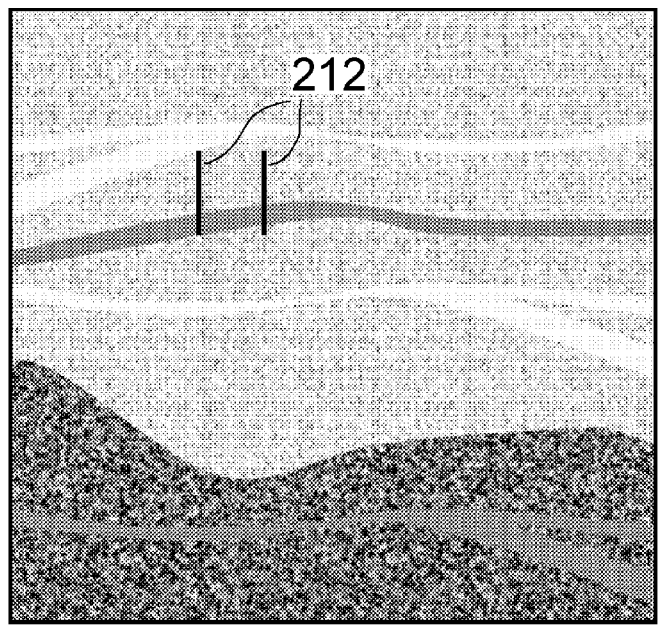

The image processing system 007 superposes the inputted position information onto a tomographic image, and transmits the result to the image display device 008. FIG. 10A and FIG. 10B are display examples of position information obtained by a correlation change position extraction unit, and illustrate examples in which a position outputted by the correlation change position extraction unit 010 is displayed in the form of markers such as an arrow 211, segment 212 or the like. Also, the detected position that is presented to the operator may involve, for instance, changes in the hue of the tomographic image, circling of images, and the like.

Figure 11A:
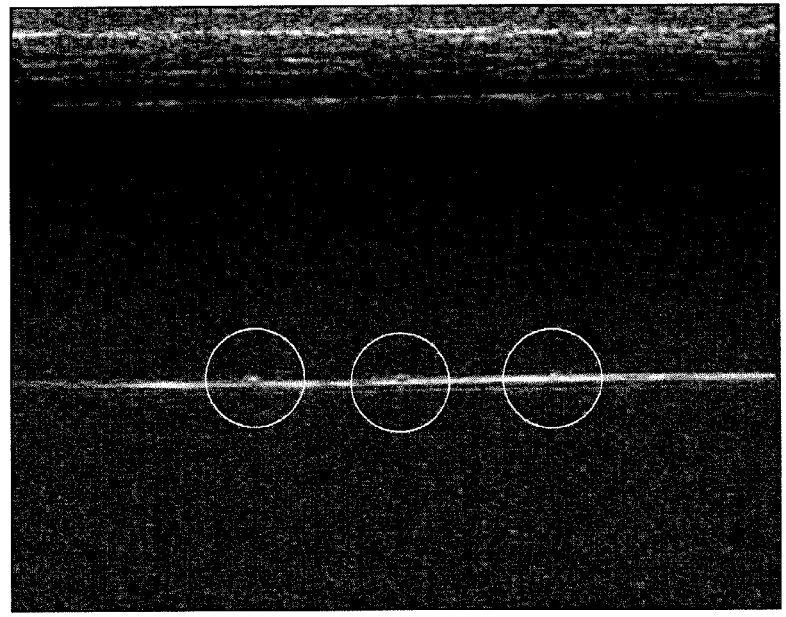
FIG. 11A and FIG. 11B are diagrams of plots of signal intensity and correlation values, respectively.

The effect of the present embodiment will be explained next with reference to FIG. 11 and FIG. 12. FIG. 11A illustrates the imaging result of ultrasound transmission and reception in an instance where there are arranged a thin film that mimics a layered tissue, in a phantom that mimics an organism, plus three wires that mimic high-reflection bodies. The three high-reflection bodies are present in the vicinity of the centers of the white circles in the figure.

Figure 11B:
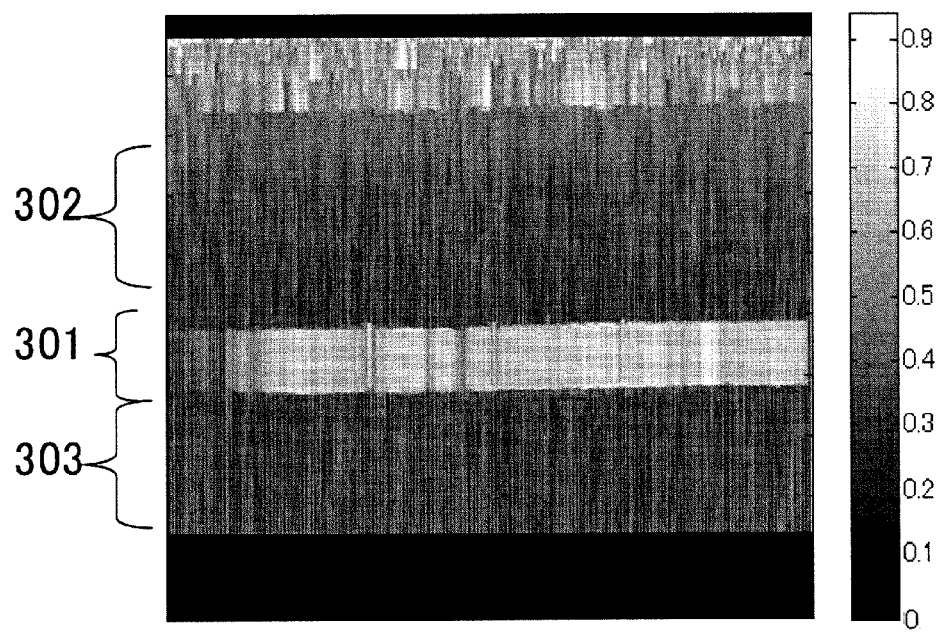

FIG. 11B illustrates the results obtained by the inter-scanline correlation calculation unit 009 for correlation value between adjacent scanlines in the observation region.

It is found that the correlation value in region 301, which comprises layered tissue, is high, while the correlation values in regions 302, 303, where layered tissue is absent, are comparatively low. The spectral pattern of regions 302, 303 is dominant, and there is no target of comparatively strong reflected ultrasound waves, for instance layered tissue or the like. Therefore, the correlation value takes on a low value, even though it is a correlation value between adjacent scanlines.

Figure 12A:
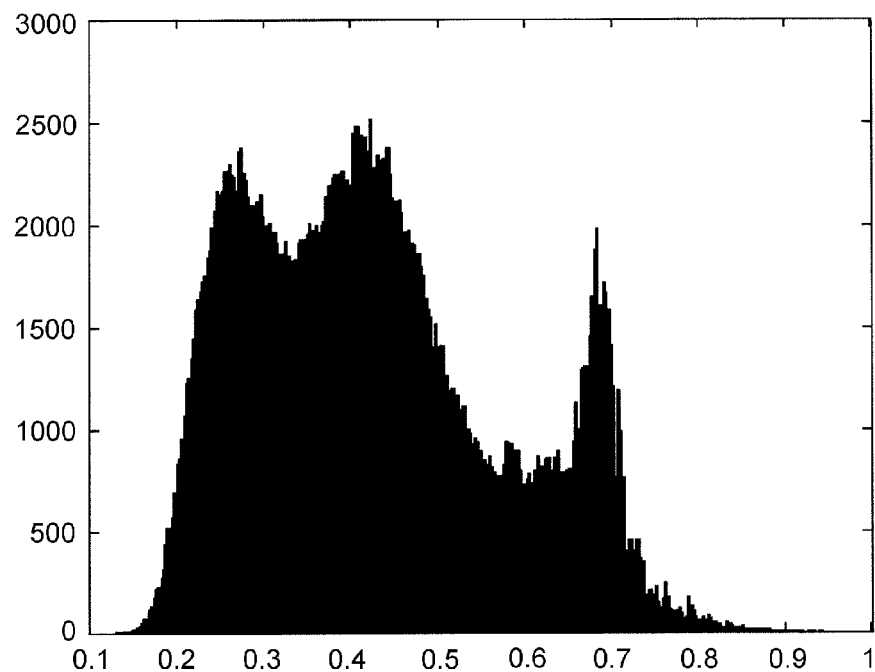
FIG. 12A and FIG. 12B are diagrams illustrating histograms of correlation values.

FIG. 12A is a histogram of all correlation values within the observation region. These correlation values include the abovementioned correlation values of regions 302, 303. Corresponding position information, as well as the correlation values such as those described herein, are outputted to the correlation change position extraction unit 010.

The signal intensity screening unit calculates signal intensity on the basis of received waveform data, and outputs information on a position (high intensity position) at which high-level signal intensity is shown.

Figure 12B:
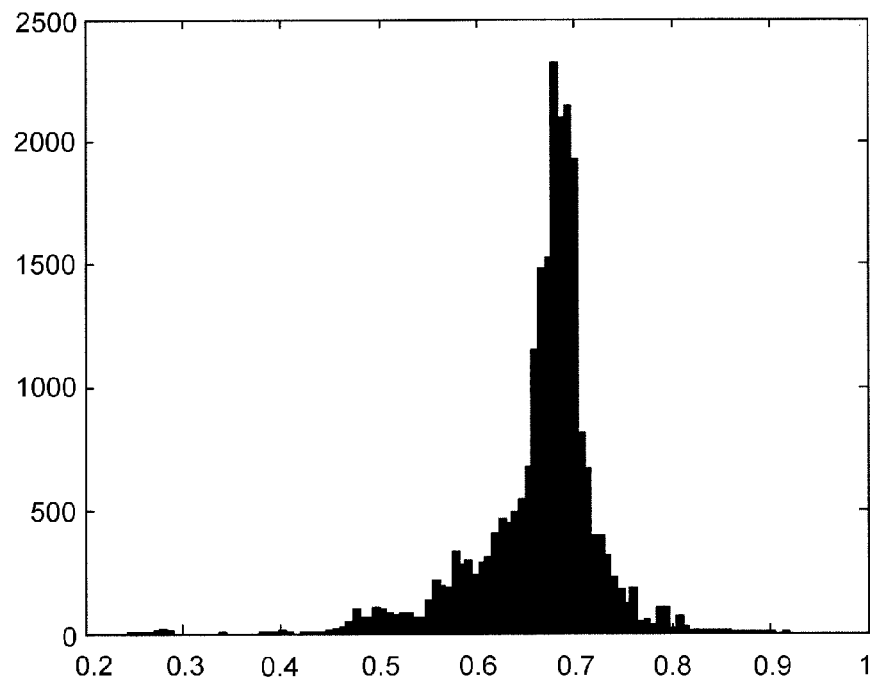

The correlation change position extraction unit 010 extracts only correlation values of regions that encompass positions that are inputted by the signal intensity screening unit 011, from among the inputted correlation values. FIG. 12B illustrates an example of a histogram of correlation values thus extracted. A comparison between the histograms in FIG. 12A and FIG. 12B reveals a significant decrease in portions of low correlation value. This indicates that low correlation values are calculated at regions where no layered tissue or high-reflection body is present, for instance regions 302, 303 in FIG. 11B.

Using position information from the signal intensity screening unit 011 allows excluding low-correlation values, unrelated to the high-reflection body, in the correlation change position extraction unit 010. The correlation change position extraction unit 010 outputs position information having a lower correlation value than a set value (second predetermined value), from among extracted correlation values. As the set value there can be used, for instance, a value resulting from subtracting an X-multiple of the standard deviation from the mean value of the extracted correlation values. Findings by the inventors have revealed that the value of X ranges preferably from 1 to 3, but the effect of the present invention can be achieved for values other than those.

The value of X can be modified to a value inputted via a separate control screen. The smaller the value of X is, the higher the sensitivity with which a high-reflection body can be detected. The larger the value of X is, the higher the specificity with which the high-reflection body can be detected.

In the present embodiment, correlation values are calculated for all data in an observation region, and there is further extracted a position at which high-level signal intensity is shown, but the present invention can be used also for one portion within the observation region.

When a transmission beam is focused onto the vicinity of a position at which a high-reflection body is present, the influence exerted by the high-reflection body becomes yet stronger, and the correlation value varies (drops) significantly. Accordingly, candidate positions of a high-reflection body can be extracted with higher precision by extracting a candidate position of the high-reflection body, and, thereafter, setting the transmission focus to the vicinity of that candidate position.

In the present embodiment, as explained above, there is calculated a correlation value of received waveform data of adjacent scanlines, and there are processed correlation values of regions corresponding to information on a position at which high-level signal intensity within a observation region is shown; a candidate of a position at which the high-reflection body is present can be extracted thereby.

Embodiment 2

In Embodiment 2 below, an example is explained of an instance where cross-correlation between scan lines are obtained based on position information from a signal intensity screening unit.

Figure 13:
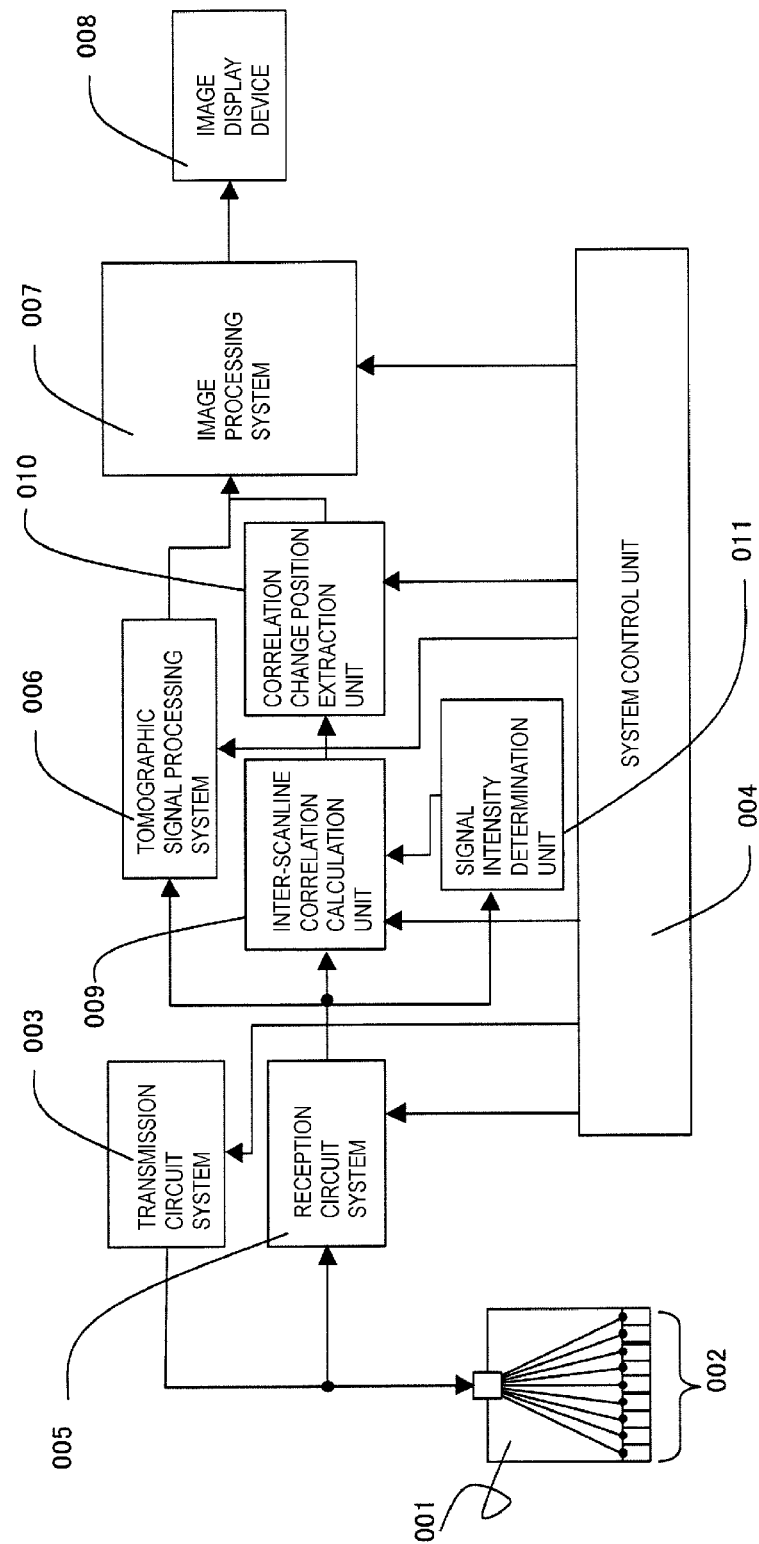
FIG. 13 is a block diagram of an ultrasound device of Embodiment 2 of the present invention.

FIG. 13 illustrates schematically a system in the present embodiment. The explanation will focus on portions dissimilar from those of Embodiment 1.

The signal intensity screening unit 011 extracts a position at which high-level signal intensity is shown at a proportion established separately, from among signal intensities in the image capture region, and outputs the position information to the inter-scanline correlation calculation unit 009. The inter-scanline correlation calculation unit 009 obtains a cross-correlation between scan lines using received waveform data inputted via the reception circuit system 005 and position information inputted via the signal intensity screening unit 011. In this case, the cross-correlation between scan lines are calculated using only received waveform data of a region corresponding to a position denoted by the inputted position information. The calculated correlation values are outputted, together with corresponding position information, to the correlation change position extraction unit 010.

The process in the correlation change position extraction unit 010, as well as subsequent processes, are identical to those of Embodiment 1. In the signal intensity screening unit 011 there is outputted information on a position at which high-level signal intensity in the image capture region is shown, typically information on a position at which the top 10% or above of the signal intensity is shown. Accordingly, the inter-scanline correlation calculation unit 009 need only calculate inter-scanline correlation for regions of 10% or less, within the image capture region. Computation for obtaining inter-scanline correlations involves large-scale computation. The present embodiment, in which there need only be obtained correlation in a partial region, allows providing an ultrasound device that is lower in cost and that makes for a more compact system, as compared with an instance where correlation is obtained for all image capture regions.

Embodiment 3

In Embodiment 3 below an example is explained of an instance where there is used not only high-level signal intensity within an observation region, but also signal intensity inside the correlation window.

Figure 14:
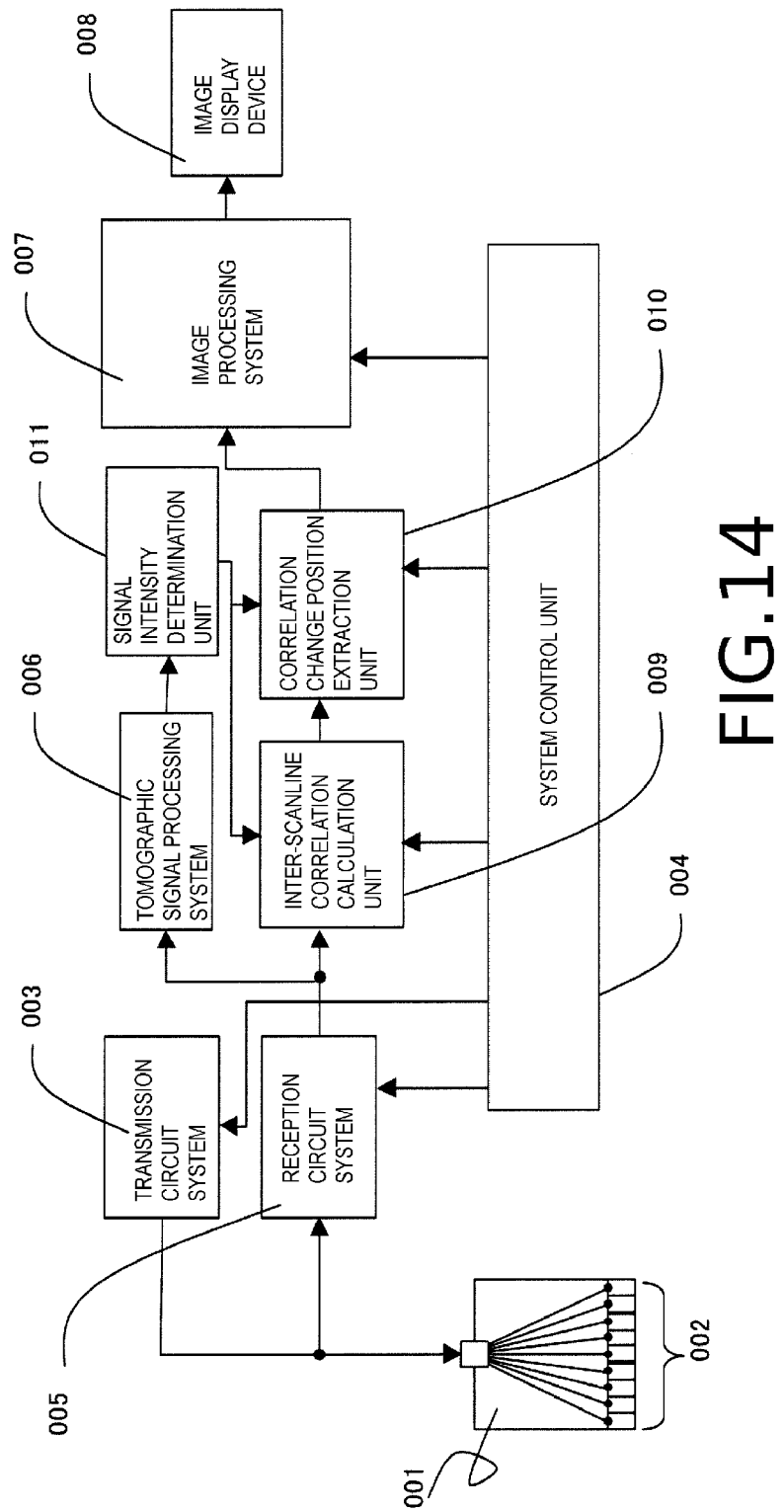
FIG. 14 is a block diagram of an ultrasound device of Embodiment 3 of the present invention.

FIG. 14 is a system schematic diagram of an ultrasound device according to Embodiment 3 of the present invention. The explanation will focus on portions dissimilar from those of Embodiment 1 and Embodiment 2.

A tomographic signal processing system 006 calculates a data envelope. Intensity data of this envelope is outputted, as signal intensity data, to the signal intensity screening unit 011. The signal intensity screening unit 011 outputs, to the inter-scanline correlation calculation unit 009, information on a position, within an observation region, at which high-level signal intensity is shown. Further, the signal intensity screening unit 011 outputs, to the correlation change position extraction unit 010, a smallest threshold value signal intensity It from among high-level signal intensities.

The inter-scanline correlation calculation unit 009 calculates cross-correlation between scan lines using received waveform data of a region corresponding to a position denoted by the inputted position information. Powers $P_1(z_1)$ and $P_2(z_1)$ given by Equation (2) and Equation (3) are worked out to calculate the correlation values. These correlation value as well as powers $P_1(z_1)$ and $P_2(z_1)$ are outputted to the correlation change position extraction unit 010.

[Math. 2]

$$P_1(z_1) = \sqrt{\sum_{z'=z_1}^{z_2} |S_1(z')|^2} \quad (2)$$

-continued

[Math. 3]

$$P_2(z_1) = \sqrt{\sum_{z'=z_1}^{Z_2} |S_1(z')|^2} \quad (3)$$

Thus, the correlation change position extraction unit 010 receives the input of the threshold value signal intensity It as well as position information having high-level signal power, from the signal intensity screening unit 011, and the correlation values and powers $P_1(z_1)$ and $P_2(z_1)$, from the inter-scanline correlation calculation unit 009.

The correlation change position extraction unit 010 extracts only position correlation values that satisfy Equation 4.

[Math. 4]

$$\sqrt{P_1(z_1) \times P_2(z_1)} > \alpha I_t \quad (4)$$

Herein, $\alpha$ is an arbitrary constant greater than 1.

The mean value and standard deviation of the correlation values are calculated using correlation values that satisfy the above condition. A reference value of correlation values is set using the mean value and the standard deviation, and position information having a correlation value equal to or smaller than the reference value is outputted to the image processing system 007.

Results obtained upon carrying out a process such as the above-described one are explained below. The left side of Equation (4) is the geometric mean of power values within a division for which there is calculated the correlation between two scanlines. An instance wherein the geometric mean value becomes equal to or greater than a constant multiple of the threshold value signal power It outputted by the signal intensity screening unit 011 is deemed to indicate that comparatively strong reflected ultrasound waves exist in either of the two scanlines, or that a plurality of layered tissues is present within the division for which the correlation is worked out. For the correlation values that are worked out at a position that satisfies Equation (4), there are preferentially extracted correlation values at high-SN ratio regions and regions that encompass reflection waveforms from layered tissue. Extracting correlation values this way allows obtaining the mean value and standard deviation of the correlation values yet more stably, with good precision. That is, it becomes possible to extract stably, and with greater precision, candidate positions for the presence of a high-reflection body.

The geometric mean and threshold value signal power are compared in the present embodiment, but the arithmetic mean or some other process may be used herein.

Embodiment 4

In Embodiment 4 an instance is explained in which candidate positions of a high-reflection body are extracted with yet better precision using position information from the correlation change position extraction unit.

Figure 15:
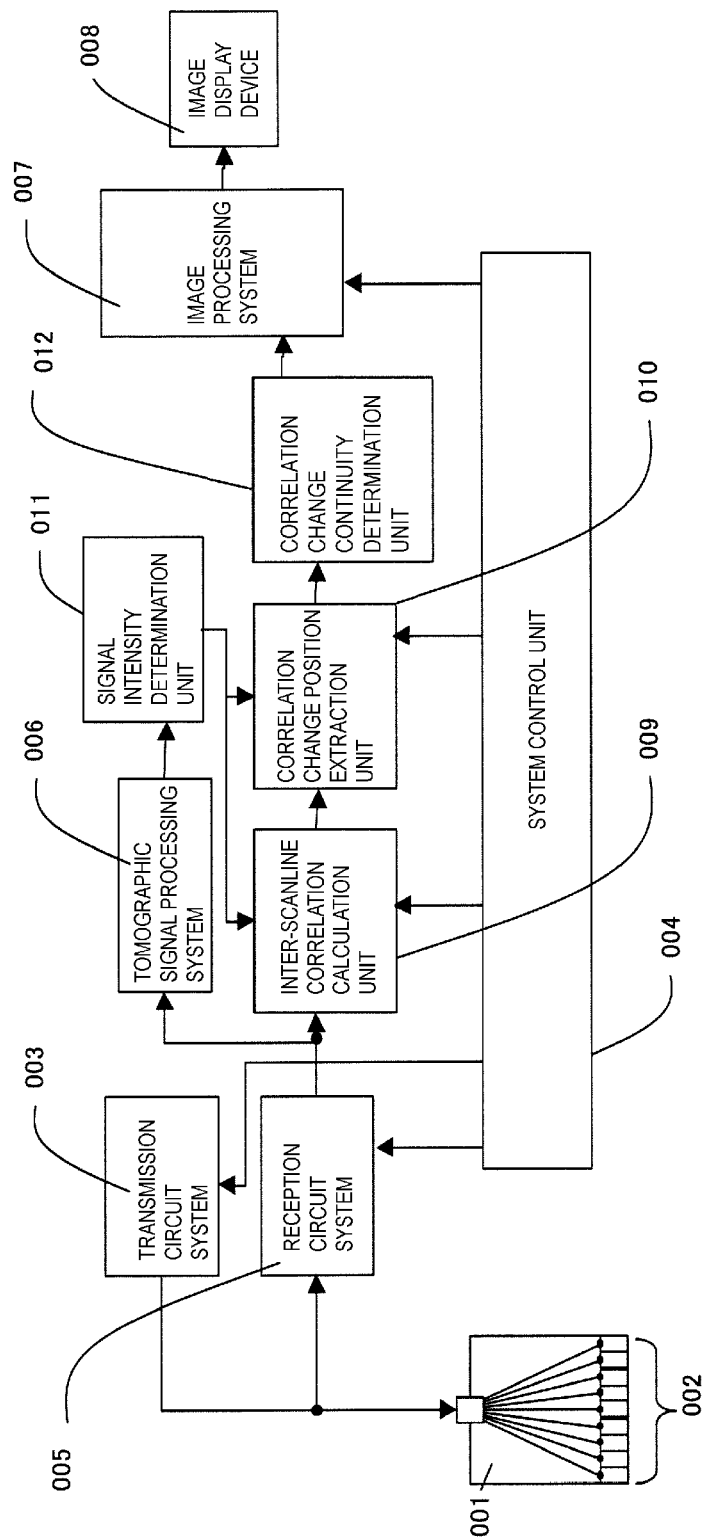
FIG. 15 is a block diagram of an ultrasound device of Embodiment 4 of the present invention.

FIG. 15 is a system schematic diagram of an ultrasound device according to Embodiment 4 of the present invention.

The explanation will focus on portions dissimilar from those of Embodiment 3.

Position information obtained according to a process identical to that of Embodiment 3 is outputted by the correlation change position extraction unit 010, and is inputted to a correlation change continuity determination unit 012. In the correlation change continuity determination unit 012 there is determined how much position information outputted by the correlation change position extraction unit 010 is present in a division width (plurality of constant-width divisions) that is used for calculating correlation values that include the inputted position information. If the proportion of position information exceeds a set value, the correlation change continuity determination unit 012 outputs, as a candidate of a position at which a high-reflection body is ultimately present, position information thereof, to the image processing system 007. The correlation change continuity determination unit corresponds to the continuity determination unit of the present invention.

Figure 16A:
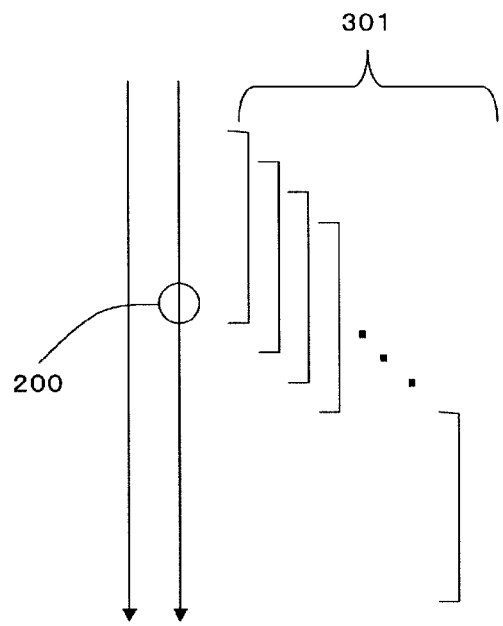
FIG. 16A and FIG. 16B are diagrams for explaining the effect of Embodiment 4.

FIG. 16 is a diagram for explaining the effect of the present embodiment. In a case where a high-reflection body 200 is present at one of adjacent scanlines, as in FIG. 16A, a division within which adjacent cross-correlation between scan lines are obtained is shifted, as indicated by the reference numeral 301, to sequentially calculate respective correlation values. In this case, the correlation values exhibit low values during the time over which the high-reflection body is included in the division where correlation values are obtained. That is, there is a high proportion of position information, outputted by the correlation change position extraction unit 010, that is present within the division width that encompasses a position of high signal intensity (in this case, position of a high-reflection body).

Figure 16B:
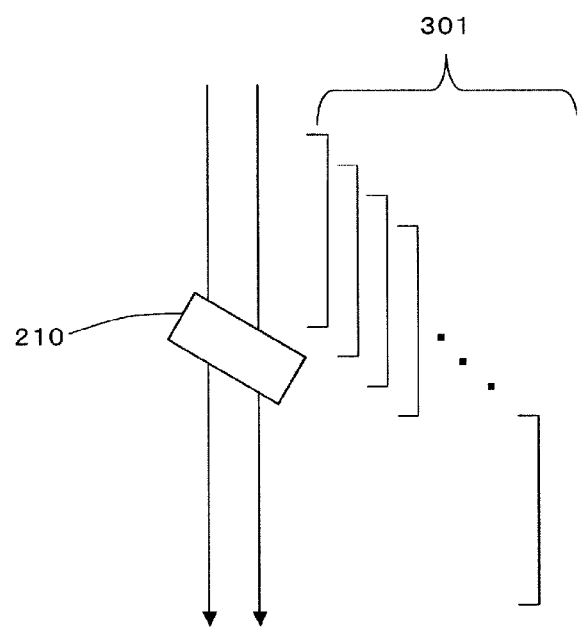

Next, there are calculated respective correlation values by shifting, as indicated by the reference numeral 301, the division in which adjacent cross-correlation between scan lines are obtained, as illustrated in FIG. 16B, in an instance where layered tissue 210 is slantingly present between two adjacent scanlines. In this case, a situation arises wherein the layered tissue 210 is present in the division in which single-scanline correlation values are obtained, but no layered tissue is present at the division of the other scanline. The correlation value takes on a low value in such a case. However, a correlation value is calculated when the layered tissue 210 is included in either of the two scanline divisions. That is, some low-correlation values plus mostly high-correlation values are found in a division width that encompasses a position of high signal intensity (in this case, a position that encompasses a layered tissue). In other words, there is a low proportion of position information outputted by the correlation change position extraction unit 010.

As a result, candidates of positions at which a high-reflection body is present can be extracted with yet better precision by determining, by way of the correlation change continuity determination unit 012, that there is high proportion of position information as outputted by the correlation change position extraction unit 010, within a division width.

Findings by the inventors have revealed that, preferably, the set value (third predetermined value) of this proportion is 50% or greater. Setting this proportion to be high makes for enhanced specificity in high-reflection body extraction, while setting the portion to be low makes for enhanced sensitivity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-022776, filed on Feb. 4, 2011, which is hereby incorporated by reference herein in its entirety.

The invention claimed is:

1. A signal processing apparatus, comprising:
a transducer that scans an elastic wave beam through an interior of an object and acquires received waveform data of a plurality of scanlines;
an intensity screening unit that calculates signal intensities on the basis of the received waveform data of the plurality of scanlines, and outputs, as a high intensity position, a position at which a calculated signal intensity is higher than a first predetermined value;
a correlation calculation unit that selects, from among the plurality of scanlines, a first scanline and a second scanline having a predetermined correlation with the first scanline, and that calculates a correlation value between received waveform data of the first scanline and the second scanline, at a plurality of constant-width divisions;
a position extraction unit that extracts, as a candidate position at which a singular region is likely to be present, a position corresponding to the high intensity position outputted by the intensity screening unit, at a division where the correlation value is lower than a second predetermined value; and
an image processing unit that performs signal processing for generating image data of the object from the received waveform data of the plurality of scanlines.

2. The signal processing apparatus according to claim 1, wherein said correlation calculation unit calculates only a correlation value in a division including a position that corresponds to the high intensity position outputted by said intensity screening unit.

3. The signal processing apparatus according to claim 1, wherein the first predetermined value is a value that is within 10% from the top of the calculated signal intensities.

4. The signal processing apparatus according to claim 1, wherein said position extraction unit determines the second predetermined value using a mean value and standard deviation of correlation values that are calculated by said correlation calculation unit.

5. The signal processing apparatus according to claim 4, wherein
said intensity screening unit outputs, as a threshold value signal intensity, a smallest signal intensity from among signal intensities that are higher than the first predetermined value;
said correlation calculation unit calculates, in addition to the correlation value, signal power of the first scanline and the second scanline included in the constant-width division; and
said position extraction unit determines the second predetermined value using only a correlation value selected according to a predetermined condition that uses the calculated signal power and the threshold value signal intensity.

6. The signal processing apparatus according to claim 1, further comprising:
a continuity determination unit that extracts, from among candidate positions extracted by said position extraction unit, a position candidate for which there exists another candidate position, at a higher proportion than a third predetermined value, in a division corresponding to the extracted candidate position.

7. The signal processing apparatus according to claim 1, wherein the predetermined correlation between the first scanline and the second scanline has a correlation value of 0.5 or greater between the first scanline and the second scanline.

8. The signal processing apparatus according to claim 1, wherein the first scanline and the second scanline are adjacent to each other.

9. The signal processing apparatus according to claim 1, wherein said image processing unit displays the candidate position superposed on an image of the object.

10. The signal processing apparatus according to claim 1, wherein a transmission beam is formed in such a manner that a transmission focus matches the candidate position, and received waveform data based on the transmission beam is used for calculation of a correlation value performed by said correlation calculation unit.

11. The signal processing apparatus according to claim 1, wherein the singular region is a region, inside the object, that constitutes a high-reflection body for elastic waves.

12. The signal processing apparatus according to claim 11, wherein the singular region is a calcified region having a diameter of 2 mm or less in an approximation when the singular region has a spherical shape.

13. The signal processing apparatus according to claim 1, wherein the second predetermined value is a value resulting from subtracting an X-multiple of a standard deviation of the correlation values from a mean value of the correlation values, wherein X is a value ranging from 1 to 3.

14. The signal processing apparatus according to claim 6, wherein the third predetermined value is 50% or greater.

15. The signal processing apparatus according to claim 5, wherein the predetermined condition is $$\sqrt{P_1 \times P_2} > \alpha I_t,$$

where $\alpha$ is a constant greater than 1, $I_t$ is the threshold value signal intensity, $P_1$ is the signal power of the first scanline, and $P_2$ is the signal power of the second scanline.

* * * * *